United States Patent [19]

Credner et al.

[11] 4,052,213
[45] Oct. 4, 1977

[54] LIGHT-SENSITIVE PHOTOGRAPHIC MATERIAL

[75] Inventors: Hans Heinrich Credner, Hohenschaeftlarn; Wolfgang Lässig; Ernst Meier, both of Munich; Erwin Ranz, Leverkusen; Siegfried Schleger, Munich; Karl-Wilhelm Schranz, Odenthal-Hahnenberg, all of Germany

[73] Assignee: AGFA-Gevaert Aktiengesellschaft, Leverkusen-Bayerwerk, Germany

[21] Appl. No.: 721,086

[22] Filed: Sept. 7, 1976

[30] Foreign Application Priority Data

Sept. 13, 1975 Germany .................................. 2540959

[51] Int. Cl.$^2$ ..................... G03C 5/30; G03C 1/06

[52] U.S. Cl. .......................................... 96/66.3; 96/95
[58] Field of Search ............ 96/66.3, 66 R, 3, 29 R, 96/95

[56] References Cited

U.S. PATENT DOCUMENTS 3,961,959  6/1976  Fujiuhara et al. ................. 96/66.3

Primary Examiner—Mary F. Kelley
Attorney, Agent, or Firm—Connolly and Hutz

[57] ABSTRACT

Oxazolinone-2 derivatives having a releasable mercapto group in their 5-position are provided as development-inhibitor-releasing thioether compounds for use in color photographic material having a high reactivity on chromogenic development of color photographic material, and are very easy to prepare.

7 Claims, No Drawings

LIGHT-SENSITIVE PHOTOGRAPHIC MATERIAL

This invention relates to new thioether compounds for use in the development of photographic silver halide materials and photographic materials containing compounds which react with oxidation products of color developer substances to release development inhibiting substances.

The incorporation in photographic materials of compounds which release development inhibitors when they react with color developer oxidation products is already known. Compounds of this kind include, for example, the so-called DIR coupler (DIR = development — inhibitor — releasing) which have been described in U.S. Pat. No. 3,227,554 and the so-called DIR compounds described in U.S. Pat. No. 3,632,345.

The aforesaid DIR couplers and DIR compounds contain a thioether substituent in the coupling position. When the color coupling reaction takes place, this substituent is split off as a diffusible mercapto compound which has development inhibiting properties and is therefore capable of influencing the subsequent development of silver halide. These DIR couplers improve the properties of photographic materials in several respects. They are capable of controlling the graininess, sharpness and gradation of the image and thereby substantially improving the color reproduction as a whole. Reference may be made in this connection to the article entitled "Development — Inhibitor — Releasing Couplers in Color Photography" in "Photographic Science and Engineering" 13,74 (1969).

The known DIR couplers inevitably release a dye together with the development inhibitor. The known DIR compounds such as those given in the U.S. Pat. No. 3,632,345, or those in U.S. Pat. Nos. 3,985,993 and 3,961,959, do not release any colored compounds in their reaction with oxidized color developers.

It has been shown, however, that under certain processing conditions the known DIR compounds are either too unstable or insufficiently reactive. In the former case, development inhibitor is not released in accordance with the image. This is demonstrated by a general loss of sensitivity. In the latter case, on the other hand, the inhibitor is split off too slowly and is therefore unable to have sufficient effect on the development process.

The known DIR couplers and DIR compounds are generally not sufficiently reactive to influence the gradation, graininess, sharpness and interimage effects to the desired extent, if they are sufficiently stable in the photographic layers to effect imagewise release of the development inhibitor.

It is therefore an object of the present invention to provide new compounds which, when they react with colour developer oxidation products, release development inhibitor substances which are sufficiently reactive to achieve, in particular, a high edge effect, straightening of the gradation curve and interimage effect but are at the same time sufficiently stable and, not least, have the advantage of being easily prepared.

This problem was solved in a highly satisfactorily manner by oxazolinone-2 compounds which contain a releasable mercapto group in the 5-position.

It is therefore one object of the present invention to provide a photographic material containing, in at least one silver halide emulsion layer or in an associated light insensitive layer of binder a preferably non-diffusible thioether compound which reacts with the oxidation product of a color developer substance containing a primary aromatic amino group to release a diffusible mercaptan which inhibits the development of silver halide.

The material is characterized in that the thioether compound contained in it is an oxazolinone-2 compound from which a mercapto group can be split off from its 5-position. The compounds to be used according to the invention may be substituted by any organic groups in its 4-position, in particular groups which are linked to the 4-position of the oxazolinone ring by a carbon atom.

The carbon atom may be saturated or unsaturated, that is to say it may be a carbon atom of an aliphatic or aromatic group. The carbon atom may be, for example, part of a carbonyl double bond, an olefinic or aromatic C=C double bond or an aromatic C=N double bond or a saturated, aliphatic group and it is preferably substituted with not more than one hydrogen atom.

The above mentioned aliphatic groups include cycloaliphatic and saturated or partially saturated heterocyclic groups while the above mentioned aromatic groups include heteroaromatic groups.

Particularly suitable compounds used according to the invention are represented by the following formula I or its tautomeric form:

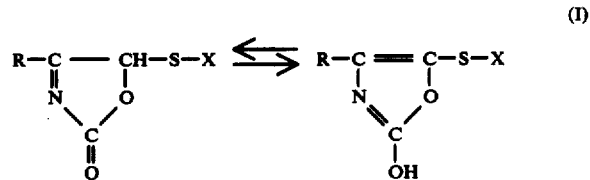

(I)

in which
X represents an aliphatic group, an aromatic group or, in particular, a heterocyclic group such that when it is split off together with the sulfur atom of the thioether bridge it forms a diffusible mercapto compound which inhibits the development of silver halide;

R represents an aliphatic, aromatic or heterocyclic group, which may be substituted, these groups being preferably linked to the 4-position of the oxazolinone-2 ring by way of a saturated or aromatic carbon atom.

Examples of aliphatic groups which X may represent include alkyl groups which may be carboxyl and/or amino substituted and having 1 to 10 carbon atoms, such as —$CH_2$—COOH and

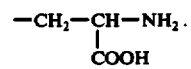

Examples of aromatic groups which X may represent include phenyl or naphthyl groups which may be substituted such as phenyl itself, carboxyphenyl and nitrophenyl.

Examples of heterocyclic groups which X may represent include:

5- and 6-membered heteroaromatic groups containing at least one nitrogen atom, e.g.
tetrazolyl such as 1-phenyltetrazolyl, 1-nitrophenyltetrazolyl and 1-naphthyltetrazolyl;

triazolyl such as 1-phenyl-1,2,4-triazolyl;
thiadiazolyl such as 2-phenylamino-1,3,4-thiadiazolyl; oxadiazolyl;
thiazolyl including benzothiazolyl and naphthothiazolyl; oxazolyl, including benzoxazolyl and naphthoxazolyl, for example 7-sulphonaphtho[2,3-d]-oxazolyl;
pyrimidyl such as 4-methyl-6-aminopyrimidyl and 4-methyl-6-hydroxypyrimidyl and triazinyl such as thiadiazolotriazinyl.

Examples of aliphatic groups which R may represent include alkyl groups having from 1 to 18 carbon atoms which may be straight or, preferably, branched chain or cyclic, and may be substituted by alkoxy, aroxy, aryl, halogen, carboxy or sulpho groups, for example cyclohexyl, methyl, isopropyl, dodecyl, benzyl, phenethyl, carboxy tert.-butyl and methoxypropyl. The alkyl groups preferably have from 3 to 18 carbon atoms and the carbon atom attached in the 4-position is preferably a branched carbon atoms, e.g. a secondary or tetriary carbon atoms, or a carbon atom which is substituted by one or two substituents, so that the alkyl group on the carbon atom carries at the most one hydrogen atom.

Examples of aromatic groups for which R may stand include phenyl or naphthyl groups which may be substituted by one or more substituents, for example by alkyl, alkoxy, alkylamino or alkylthio groups, in any of which groups the alkyl portion may contain from 1 to 20 carbon atoms; by nitro groups or by halogen such as chlorine or bromine; by carboxyl or sulpho groups; by acyl or acylamino groups in either of which the acyl portion may be derived from carboxylic acid monoesters or aliphatic or aromatic carboxylic or sulphonic acids such as heptadecyl carbonamido; dimethylaminosulphonylphenyl; octadecylaminosulphonyl; methyloctadecylaminocarbonyl; phenylaminocarbonyl; benzoylaminophenoxycarbonyl or ethoxycarbonyl. The following are specific examples: 4-t-butyl-phenyl; 3,5-di-tert.-butyl-4-oxyphenyl; 2-tetradecyl-oxyphenyl; 4-cetylmercaptophenyl; 4-N,N-di-n-butylamino-phenyl; 4-N,N-methyloctadecylamino-phenyl; 4-tetradecyl-sulphonylphenyl; 2-chloro-5-docecanoylaminophenyl; 3-(2,4-di-tert.-pentyl-phenoxyacetamino)-phenyl; 3-methoxy-4-tetradecyloxy-phenyl; 3-cetyloxyacylaminophenyl; 3-(α-sulphostearoylamino)-phenyl; 4-(4-tetradecyloxyphenylsulphonamino)-phenyl and 3-tetradecanoylaminophenyl.

Examples of heterocyclic groups which R may represent include
5- or 6-membered heterocyclic groups, in particular heteroaromatic groups having at least one nitrogen atom, e.g. pyridyl; thiazolyl; morpholino; furanyl or indole groups, for example N-octylindolyl.

Compounds in which R contains a photographically inert group which confers diffusion resistance are preferred.

Compounds which are not diffusion resistant may be added to one or more layers or to the developers to improve the graininess and fog.

Groups are regarded as conferring diffusion resistance if they make it possible for the compounds according to the invention to be incorporated in a diffusion-fast form in the hydrophilic colloids normally used in photographic materials. The most suitable groups for this purpose are organic groups, which may generally contain straight or branched chain aliphatic groups and may also contain isocyclic or heterocyclic aromatic groups. The aliphatic portion of these groups generally contains from 8 to 20 carbon atoms. These groups are attached to the remainder of the molecule either directly or indirectly, e.g. by way of one of the following groups: —CONH—, —SO$_2$NH—, —CO—, —SO$_2$—, —O—, —S— or —NR'— in which R' represents hydrogen or alkyl.

The group which confers diffusion resistance may, in addition, contain water-solubilizing groups, e.g. sulfo groups or carboxyl groups, and these may also be present in an anionic form. Since the diffusion resistance depends on the molecular size of the compound as a whole, it is in certain cases sufficient, for example if the whole molecule is sufficiently large, to use one or more shorter chain groups for conferring diffusion resistance, e.g. t-butyl, cyclopentyl or isoamyl groups.

Compounds of the above formula which have proved to be particularly suitable are those in which R represents, phenyl which may be substituted with one or more alkyl, alkoxy, cycloalkyl or acyl groups which may be derived from carbonic acid monoesters or from aliphatic or aromatic carboxylic or sulphonic acids, for example benzoyl; sulfonyl alkylaminosulfonyl alkoxycarbonyl; phenoxycarbonyl or alkylaminocarbonyl groups.

Compounds of the above formula in which X represents a 1-phenyltetrazolyl group have proved to be particularly useful.

Some examples of the compounds to be used according to the invention are shown below:

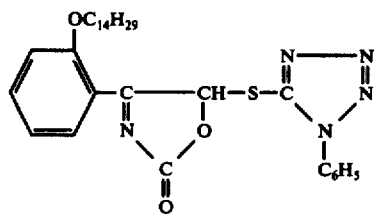

1)

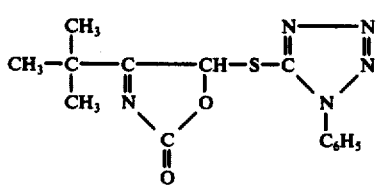

2)

3)
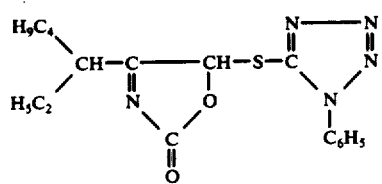
4)
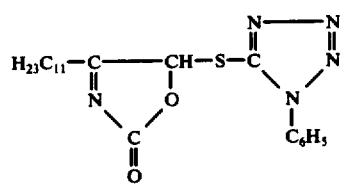
5)
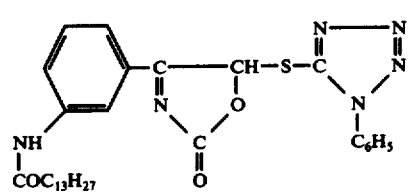
6)
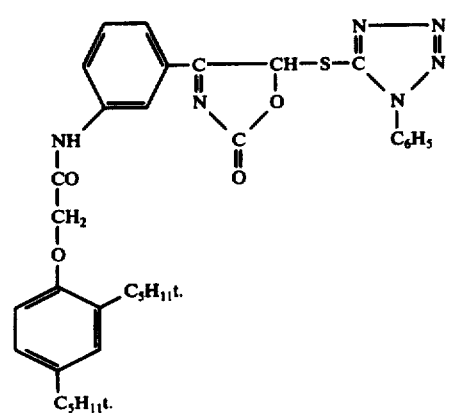
7)
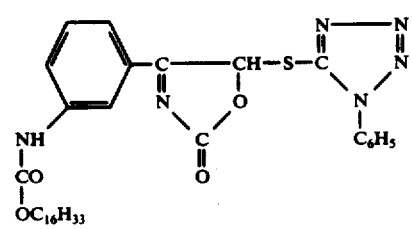
8)
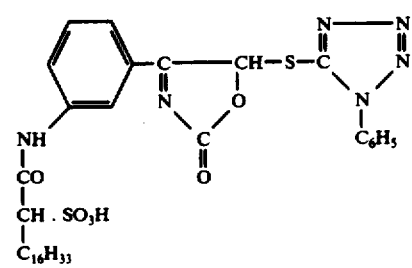
9)

-continued
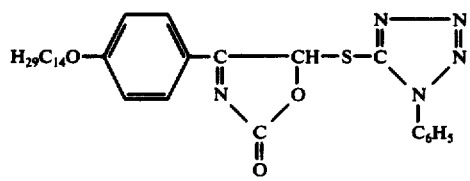
10)
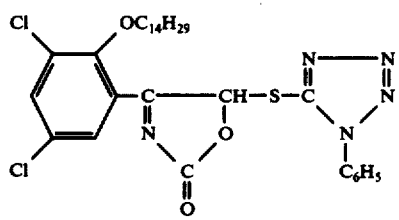
11)
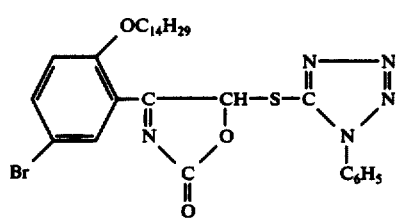
12)
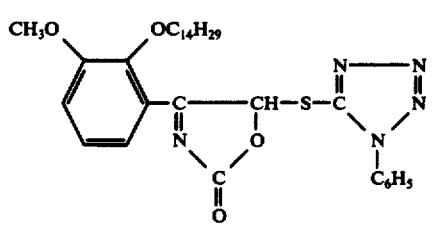
13)
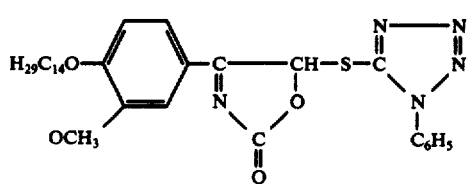
14)
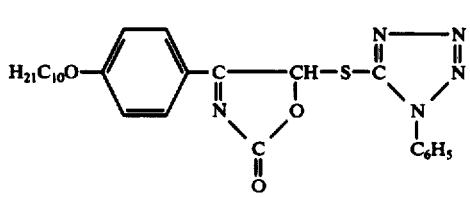
15)
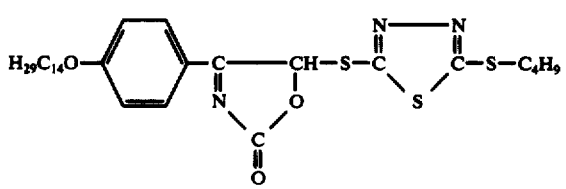
16)

-continued
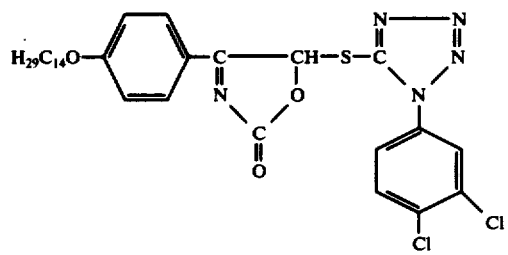
17)
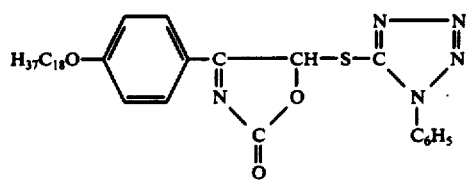
18)
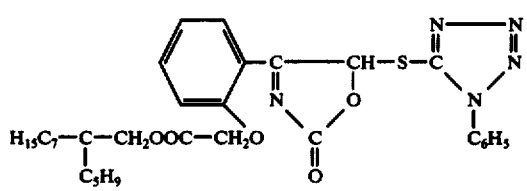
19)
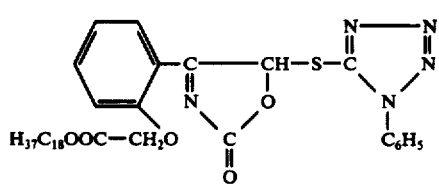
20)
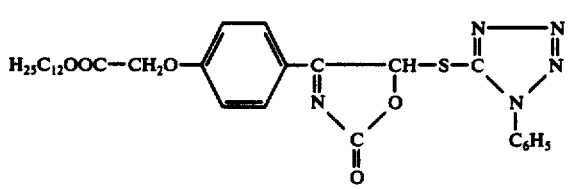
21)
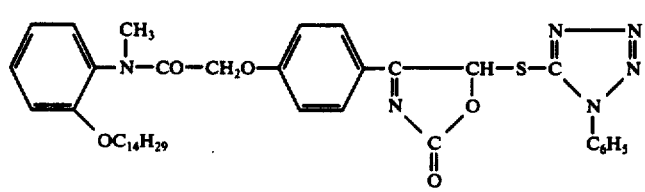
22)
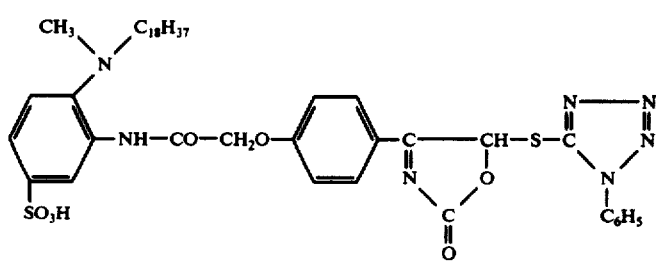
23)

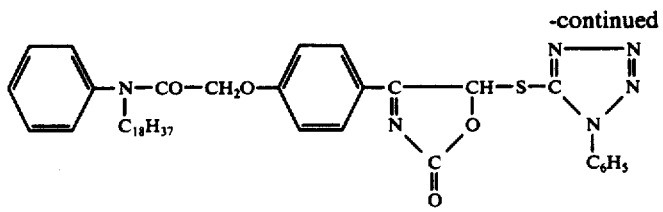

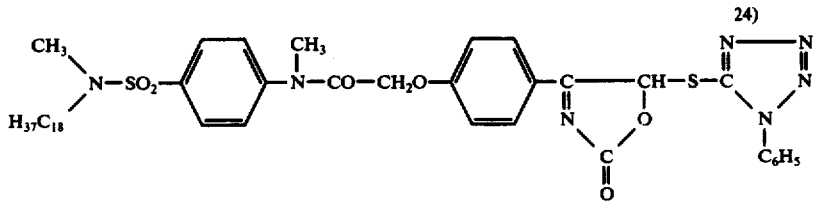

The compounds used according to the invention are prepared by the reaction of oxazolinone-2 compounds, not carrying the substituent S—X, or their tautomeric form with a solution of the sulphenyl chloride of the inhibitor in an inert solvent such as chloroform or carbon tetrachloride in a similar manner to the known method of preparation of DIR compounds.

The oxazolinone-2 compounds, not carrying the substituent S-X, required as starting material or their tautomeric form can easily be prepared from the corresponding oxazolinone-2-carboxylic acid-2-butyl esters-5 by removal of isobutene and decarboxylation.

Removal of the tertiary butyl group as isobutene, and decarboxylation, may be carried out separately or in one operation. Methods for the removal of isobutene and decarboxylation have been fully described in the literature. The following method has been found to be particularly suitable:

The corresponding oxazolinone-2-carboxylic acid tertiary butyl ester-5 compound was boiled in a high boiling solvent such as dichlorobenzene, bromobenzene or the like with the addition of a catalytic quantity of toluene sulfonic acid or in glacial acetic acid with a catalytic quantity of toluene sulfonic acid. The reaction time required depends to a large extent on the substituent in the 4-position of the oxazolinone ring and may vary from 30 minutes to 6 hours.

The corresponding oxazolinone-2-carboxylic acid tert.-butyl ester can easily be prepared by the method described in our copending British Patent Application No. 53128/75 which in the following will be described briefly again.

The corresponding β-chloro- or β-bromo- compound is prepared from α-ketocarboxylic acid t-butyl ester by known methods. The reaction of β-halogen-α-ketocarboxylic acid ester is carried out in the presence of an aprotic, preferably polar solvent, to which traces of water may be added, at a reaction temperature of from 20° to 150° C in the presence of an alkali metal cyanate such as sodium or potassium cyanate.

The aprotic solvents used may be ethers, sulfoxides, nitriles or acid amides such as carboxylic acid amides or phosphonic acid amides, preferably hexamethylphosphoric acid triamide, dimethylformamide, dimethylsulfoxide or acetonitrile, either alone or in combination.

The following general method of preparation has been found particularly suitable:

1 Mol of the β-chloro-α-keto-carboxylic acid t-butyl ester which is to be reacted is dissolved in a 5 to 10 times excess of acetonitrile and then added dropwise, with stirring, at a bath temperature of 90° to 100° C to a suspension of 3 to 5 mol of an alkali metal cyanate, preferably sodium cyanate, in 2 to 5 times its quantity of hexamethylphosphoric acid triamide, dimethylformamide or dimethylsulfoxide to which 0 to 1.5 mol of water may previously have been added.

After a further 10 to 160 minutes, the reaction mixture is taken up with a solvent such as ethyl acetate or methylene chloride and filtered from unreacted alkali metal cyanate. The reaction solution is then neutralized with glacial acetic acid and extracted several times with water or sodium chloride, depending on the solubility of the oxazolinone-2 compound in water.

The residue left after evaporation of the solvent is recrystallized from a suitable solvent.

The yields obtained are between 20 and 80 % of the theoretical yield, depending on the starting compound used.

The preparation of the compounds according to the invention is described in detail below.

PREPARATION 1 (COMPOUND) 1)

1st Stage 74 g of t-butyl alcohol, 79 g of pyridine and 250 ml of anhydrous ether were heated to their boiling temperature and 146 g of dichloroacetyl chloride were added dropwise to the reaction mixture at such a rate that the mixture continued to boil without further application of heat. The mixture was boiled for a further 3 hours after all the dichloroacetyl chloride had been added. Water was then added and the ether phase was separated. The resulting reaction mixture was processed by the usual methods.

The yield was 140 g of α,α-dichloroacetic acid t-butyl ester.

2nd Stage 18.5 g of ester obtained in Stage 1, 31.8 g of o-tetradecyloxybenzaldehyde and 70 ml of absolute ether were cooled to a temperature of −15° C with a mixture of ice and salt. 13.5 g of solid potassium t-butylate were then added to the reaction mixture in small portions. The mixture was kept at a temperature of −20° C for a further 2 hours after all the potassium t-butylate had been added and neutralized with glacial acetic acid. Water was then added to the reaction mixture. The ethereal layer was separated off and washed with water until neutral in reaction. Evaporation of the ether left an oily residue of o-tetradecyloxyphenyl-β-chloro-α-ketopropionic acid t-butyl ester which was used without further purification.

3rd Stage 18 g of urethane, 11.2 of potassium tertiary butylate and 150 ml of hexamethylphosphoric acid triamide were thoroughly stirred at a bath temperature of 140° to 150° C for 20 minutes. To the resulting mixture the residue obtained in the 2nd stage was added and the temperature was kept for 1 hour. The mixture was poured into 1 liter of water and the separating oil was taken up in ethyl acetate and several times washed with water. After evaporation of the solvent the crude residue 4-(o-tetradecyloxy)-5-tert.-butoxy-carbonyl-2-oxazolinone was used for the next stage without further purification.

20 g of the crude product obtained in Stage 3 were stirred into 20 ml of 1,2-dichlorobenzene with the addition of 0.15 g of p-toluenesulfonic acid for 1½ hours at a bath temperature of 180° C. Isobutene and carbon dioxide split off in the process. When the solution was cold, the desired product was precipitated with 100 ml of petroleum hydrocarbons boiling in the range of 50° to 75° C.

The yield was 10 g of 4-(o-tetradecyloxyphenyl)-oxazolinone-2, with a m.p. of 138° to 139° C.

5th Stage

A solution of 0.025 mol of 1-phenyl-5-tetrazolyl-sulfenyl chloride in 40 ml of glacial acetic acid was added to a solution heated to 50° of 9.3 g (0.025 mol) of the compound prepared according to Stage 4 in 60 ml of glacial acetic acid, and the mixture was stirred for 2 hours at 50° C. 100 ml of ethylene chloride were then added and the reaction solution was poured out on water. After separation of the ethylene chloride phase in the usual manner, the residue was recrystallized from a small quantity of butyl chloride. The yield was 8.5 g of compound 1, with a m.p. of 91° to 94° C.

PREPARATION 2 (COMPOUND NO. 7)

1st Stage 30 g of m-nitrophenyl-$\beta$-chloro-$\alpha$-keto-propionic acid t-butyl ester obtained by a similar method to that described in Example 1, Stage 1, were reacted with 35 g of potassium cyanate in 100 ml of hexamethylphosphoric acid triamide at 100° C with vigorous stirring to produce the desired 5-t-butoxycarbonyl-4-m-nitrophenyl-oxazolinone-2 compound having a m.p. of 76° to 78° C.

2nd Stage 15.3 g of the compound prepared in Stage 1 were reacted with 0.1 g of p-toluenesulfonic acid in 60 ml of glacial acetic acid for 3 hours at 120° to 125° C with stirring. The precipitated reaction product was suction filtered after cooling.

The yield was 9 g of 4-(m-nitrophenyl)-oxazolinone-2 with an m.p. of 222° to 225° C.

3rd Stage 9 g of the nitro compound obtained according to Stage 2 were converted into the amino compound by the usual methods using palladium on active charcoal under normal conditions. The yield was 7.8 g of 4-(m-aminophenyl)-oxazolinone-2 with an m.p. of 158° C.

4th Stage

A mixture of 3.5 g of chloroformic acid cetyl ester (92%) and 15 ml of ethylene chloride was added to a solution of 1.76 g (0.1 mol) of the compound obtained according to Stage 3 and 0.85 g of sodium acetate sicc. in 40 ml of glacial acetic acid at 50° C with stirring, and the whole mixture was then stirred for one hour. The reaction mixture was then poured out on water and the ethylene chloride layer was separated and processed in the usual manner. The residue was recrystallized from ethyl acetate.

The yield was 3.5 g of 4-(m-cetyloxacylaminophenyl)-oxazolinone-2, with an m.p. of 124° to 126° C.

5th Stage

A sulfenyl chloride solution of 0.89 g (0.005 mol) of 1-phenyl-5-mercaptotetrazole in 8 ml of glacial acetic acid was added to a solution of 2.22 g (0.005 mol) of the compound prepared according to Stage 4 in 40 ml of glacial acetic acid at 50° C and the reaction mixture was left at 40° C for 3 hours. Compound 7 precipitated when the reaction mixture was left to stand overnight, and was separated off.

The yield was 2.5 g of compound 7 with an m.p. of 136° to 137° C.

The compounds according to the invention are comparable to the known DIR couplers and DIR compounds in the following respects: Like the said DIR couplers and compounds they constitute non-diffusible thioether compounds which react with oxidation products of color developers to release a diffusible mercaptan which inhibits development of silver halide. According to U.S. Pat. No. 3,148,062, DIR couplers are subdivided into those in which the group which can be split off already has an inhibitory action before coupling and those in which the inhibitory action is not released until a molecular group is split off from the coupling position. In the latter case, the inhibitor is non-preformed. According to this terminology, most of the compounds according to the invention listed above must also be regarded as non-diffusible compounds which, when they react with color developer oxidation products, release a diffusible, non-preformed development inhibitor.

The compounds according to the invention are distinguished from the known DIR couplers and DIR compounds by their increased reactivity so that, when used in photographic materials, they can advantageously improve the control of gradation, graininess and sharpness as well as the edge and interimage effects. In addition, the DIR compounds according to the invention have the particular advantage of suppressing fogging which cannot always be prevented in conventional photographic materials without the additives according to the invention, and which is not suppressed to the same extent by the known DIR compounds and DIR couplers.

The DIR compounds according to the invention are particularly suitable for use in those photographic materials, and preferably color photographic multilayered materials, in which the silver halide, after imagewise exposure, is developed by the usual color developers, e.g. by the usual aromatic compounds based on p-phenylene diamine and containing at least one primary amino group. For controlling the graininess and sharpness, they may also be used in the usual black-and-white materials or in developer solutions used for developing both color photographic and black-and-white materials or in any processing solutions used before development, if development is carried out using a color developing substance.

The following are examples of suitable color developers:

N,N-Dimethyl-p-phenylenediamine;
N,N-diethyl-p-phenylenediamine;
monomethyl-p-phenylenediamine;
2-amino-5-diethylaminotoluene;
N-butyl-N-ω-sulphobutyl-p-phenylenediamine;
2-amino-5-(N-ethyl-N-β-methanesulphonamidoethylamino)-toluene;
N-ethyl-N-β-hydroxyethyl-p-phenylenediamine;
N,N-bis-(β-hydroxyethyl)-p-phenylenediamine; and
2-Amino-5-(N-ethyl-N-β-hydroxyethylamino)-toluene.

Other suitable color developers have been described, for example, in J. Amer. Chem. Soc. 73, 3100 (1951).

The developer compounds are generally contained in an alkaline developer bath used for treating the photographic material after it has been exposed imagewise but they may also be incorporated in one or more layers of the photographic material. In that case, the developer compounds may contain groups which confer diffusion resistance on them and they may be situated in a layer which also contains a diffusion resistant colour coupler or a diffusion resistant color producing compound, for example as described in U.S. Pat. No. 3,705,035.

All that is then required for development is an alkaline activator solution containing an auxiliary developer, for example phenidone. The oxidation product produced from the color developer when development takes place reacts with the non-diffusible color coupler to form a non-diffusible image dye or with the non-diffusible color producing compound to form diffusible dyes in imagewise distribution, and these diffusible dyes can be transferred to an image receiving layer. At the same time, the oxidation product of the color developer reacts with the non-diffusible DIR compounds according to the invention which are also present to liberate diffusible inhibitor molecules. At the same time, the remainder of the molecule of the DIR compound gives rise to a substantially colourless or slightly yellow dye which causes practically no interfering side density in the final color image.

The color photographic multilayered material according to the invention contains a compound of formula I in at least one of its layers. This DIR compound may be incorporated in a light-sensitive silver halide emulsion layer or in a hydrophilic layer of binder which is associated with such a light sensitive silver halide emulsion layer but need not itself be sensitive to light. The term "associated" is used in this context to describe a layer which is in such spatial relationship to the light-sensitive silver halide emulsion layer that significant quantities of color developer oxidation products are found in it on development of the silver halide emulsion layer due to diffusion from the light-sensitive silver halide emulsion layer.

The concentrations of the DIR compound according to the invention in the given layer may vary within the wide limits, e.g. between $0.1 \cdot 10^{-3}$ and $40 \cdot 10^{-3}$ mol per kg of silver halide emulsion while in the associated layers of binder it may vary e.g. between $0.1 \cdot 10^{-3}$ and $10 \cdot 10^{-3}$ mol per gram of binder. The concentration depends on the purpose for which the compound is to be used, on the silver halide emuslion and on whether the DIR compound is situated in a silver halide emulsion layer or in a light-sensitive layer of binder. The upper limit may advantageously be kept below the concentration at which colour couplers are used in photographic layers since the compounds according to the invention produce excellent effects even when used at low concentrations.

The concentration at which the DIR compound according to the invention is used in processing solutions such as developers depends on the desired effect, the photographic materials used and the emulsions contained in the materials, and it can easily be determined by a few laboratory tests.

The compounds according to the invention may be used in the yellow, magenta or cyan layer of color photographic multilayered materials or in a light insensitive layer adjacent to the aforesaid layers since, in modern photographic materials, high interimage effects, improvement in the graininess and increase in the sharpness by improvement of the edge effect are important in all the color producing light sensitive layers.

The inhibitory effect of the compounds used according to the invention may be produced both in the layer containing the compounds according to the invention, provided it contains developable silver halide, and in adjacent silver halide emulsion layers into which the released inhibitor is capable of diffusing. The compounds according to the invention are therefore capable of controlling development in each of the individual light-sensitive silver halide emulsion layers in various ways and moreover, by making use of the vicinal effects which can be produced by the compounds according to the invention, development of one silver halide emulsion layer can be influenced by the results of imagewise development in another layer so that an overall improvement in graininess, sharpness and color reproduction can be achieved. Another interesting application is the use of the DIR compounds according to the invention in so-called double layers of a multi-layered material. These double layers constitute a partial color unit which, for the purpose of achieving higher sensitivity and a fine grain, is composed of two layers arranged above one another in a multilayered unit, for example as described in U.S. Pat. No. 3,932,185. The double layer combination of a partial color unit generally consists of a combination of a coarse grained, high sensitivity layer containing a less than equivalent quantity of color coupler placed above a less sensitive layer containing an excess of color coupler.

For obtaining the desired effects such as graininess, improvement in sharpness and inter image effect, the DIR compounds according to the invention may be added to one or other of the two layers or to both. They are preferably added to the lower, fine grained layer of a double layer combination.

The light-sensitive silver halide emulsion layers of the photographic material according to the invention have differing spectral sensitivites and each layer has associated with it at least one non-diffusible compound for producing an image dye of a color which is generally complementary to the spectral sensitivity. These compounds may be conventional color couplers which are generally incorporated in the silver halide layers. The red-sensitive layer, for example, contains a non-diffusible color coupler for producing the cyan partial color image, generally a coupler based on phenol or α-naphthol, The green sensitive layer contains at least one non-diffusible color coupler for producing the magenta partial color image, normally a color coupler based on 5-pyrazolone or indazolone. The blue sensitive layer unit contains at least one non-diffusible colour coupler for producing the yellow partial colour image, generally a color coupler having an open chain keto methylene group. Color couplers of these kinds are known in large numbers and have been described in numerous patent specifications. Reference may be made, for example, to the publication entitled "Farbkuppler" by W. Pelz in "Mitteilungen aus den Forschungs-laboratorien der Agfa, Leverkusen/Munich", Volume III (1961) and K. Venkataraman in "The Chemistry of Synthetic Dyes," Vol. 4, 341 – 387 Academic Press 1971.

The non-diffusible color couplers may contain one releasable substituent in the coupling position so that in contrast to the usual 4-equivalent couplers they require only 2 equivalents of silver halide for color production. The color couplers as such are generally colorless but if the releasable substituent contains a chromophoric group, as in the case of the known masking couplers, then the color couplers generally have a color which is suitable for masking unwanted side densities of the image dye by the usual masking techniques. Image dyes produced from color couplers are generally diffusion resistant.

In some cases, however, the image dyes may first be produced in a diffusible form when development takes place and only subsequently fixed after transfer to an image receiving layer, as is known from various dye diffusion transfer processes, for example as described in U.S. Pat. No. 3,227,550 and No. 3,628,952 and in British patent application No. 1,243,048. In that case, colorless or colored, non-diffusible color producing compounds which release diffusible dyes in image-wise distribution when development takes place are associated with the light-sensitive silver halide emulsions. Such color producing compounds are incorporated either with the silver halide emulsion layer or with an associated hydrophilic layer of binder which may, for example, contain development nuclei and may also contain a silver halide which is developable without exposure.

When conventional silver halide emulsions are used in combination with non-diffusible color couplers or non-diffusible color producing compounds, they normally give rise to negative color images. DIR compounds according to the invention may, however, also advantageously be used in reversal processes like the DIR couplers to give rise to positive images. These positive images may be obtained either by conventional reversal processes in which the photographic material is first subjected to black-and-white development after imagewise exposure and then color developed after a diffuse second exposure or by a special reversal process in which the imagewise information in the photographic material is reversed due to the presence of the DIR compounds according to the invention. This may take place if, for example, a silver halide emulsion layer which is capable of spontaneous development, i.e. development without exposure, and which contains a color coupler or color producing compound, is arranged adjacent to a conventional silver halide emulsion layer which contains a DIR compound. It is clear that such a process requires DIR couplers or DIR compounds which release the inhibitor very rapidly so that it will inhibit development imagewise in the spontaneously developable layer.

The non-diffusible color couplers and color producing compounds as well as the non-diffusible compounds used according to the invention which release a development inhibitor are added to the light-sensitive silver halide emulsions or other casting solutions by the usual methods. If the compounds are water-soluble or alkali soluble, they may be added to the emulsions in the form of aqueous solutions, to which organic solvents which are miscible with water may be added, such as ethanol, acetone or dimethylformamide. If the non-diffusible color couplers, color producing compounds and development inhibitor releasing compounds are insoluble in water or alkalies, they may be emulsified in known manner, e.g. a solution of the compounds in a low boiling organic solvent may be directly mixed with a silver halide emulsion or the solution may first be mixed with an aqueous gelatine solution, and the organic solvent is removed in the usual manner and the resulting emulsion of the compound in gelatine is then mixed with the silver halide emulsion. Such hydrophobic compounds may be emulsified with the aid of so-called coupler solvents or oil formers which are generally higher boiling organic compounds in which the non-diffusible color couplers and development inhibitor releasing compounds which are to be emulsified in the silver halide emulsions become enclosed in the form of oily droplets as described in example, in U.S. Pat. Nos. 2,322,027; 2,533,514; 3,689,271; 3,764,336 and 3,765,897. If the compounds according to the invention are emulsified in the layers with the aid of such oil formers, less powerful groups for conferring diffusion resistance may be used in the compounds according to the invention since, in that case, shorter alkyl groups such as t-butyl or isoamyl groups are sufficient to prevent diffusion of the compounds according to the invention in the layers of the photographic material.

The present invention is suitable for any of the usual silver halide emulsions which may contain silver halide, silver chloride, silver bromide or mixtures thereof, which may have a small silver iodide content of up to 20 mols %. The emulsions may be either ordinary negative emulsions or direct positive emulsions, e.g. those which have a high sensitivity in the interior of the silver halide grains, for example emulsions of the kind described in U.S. Pat. No. 2,592,250.

The binder used for the photographic layers is preferably gelatine but it may be partly or completely replaced by other natural or synthetic binders. Suitable natural binders include e.g. alginic acid and its derivatives such as salts, esters or amides; cellulose derivatives such as carboxymethyl-cellulose; alkylcelluloses such as hydroxyethyl cellulose; starch or its derivatives such as ethers or esters or carrageenates. Suitable synthetic binders include polyvinyl alcohol, partially saponified polyvinyl acetate, and polyvinylpyrrolidone.

The emulsions may also be chemically sensitized, e.g. by the addition of sulfur compounds such as allyl isothiocyanate, allylthiourea, and sodium thiosulfate at the chemical ripening stage. Reducing agents may also be used as chemical sensitizers, e.g. the tin compounds described in Belgian Patent Specifications Nos. 493,464 and 568,687; polyamines such as diethylene triamine or aminomethane sulfinic acid derivatives, e.g. according to Belgian Patent Specification No. 547,323.

Noble metals such as gold, platinum, palladium, iridium, ruthenium or rhodium and compounds of these metals are also suitable chemical sensitizers. This method of chemical sensitization has been described in the article by R. Koslowsky, Z. Wiss. Phot. 46, 65–72 (1951).

The emulsions may also be sensitized with polyalkylene oxides derivatives, e.g. with a polyethylene oxide having a molecular weight of between 100 and 20,000 or with condensation products of alkylene oxides and aliphatic alcohols, glycols, cyclic dehydration products of hexitols, alkyl substituted phenols, aliphatic carboxylic acids, aliphatic amines, aliphatic diamines and amides. The condensation products have a molecular weight of at least 700, preferably more than 1000. These sensitizers may, of course, be combined to produce special effects as described in Belgian Patent Specification No. 537,278 and British patent specification No. 727,982.

The emulsions may also be spectrally sensitized, for example with the usual monomethine or polymethine dyes such as acid or basic cyanines; hemicyanines; streptocyanines; merocyanines; oxonols; hemioxonols; or styryl dyes or trinuclear or higher nuclear methine dyes, for example rhodacyanines or neocyanines. Sensitizers of this kind have been described, for example, in the work by F. M. Hamer entitled "The Cyanine Dyes and Related Compounds" (1964) Interscience Publishers John Wiley and Sons.

The emulsions may contain the usual stabilizers such as homopolar compounds or salts of mercury containing aromatic or heterocyclic rings, such as mercaptotriazoles, simple mercury salts, sulfonium mercury double salts and other mercury compounds. Azaindenes are also suitable stabilizers, particularly tetra- and penta-azaindenes and especially those which are substituted with hydroxyl or amino groups.

Compounds of this kind have been described in the article by Birr, Z. Wiss. Phot. 47, 2–58 (1952). Other suitable stabilizers include heterocyclic mercapto compounds, e.g. phenylmercapto tetrazole, quaternary benzothiazole derivatives and benzotriazole.

The emulsions may be hardened in the usual manner, for example with formaldehyde or halogenated adlehydes containing a carboxy group, such as mucobromic acid, diketones, methanesulphonic acid esters, and dialdehydes.

The photographic layers may also be hardened with epoxide hardeners, heterocyclic ethylene imine hardeners or acryloyl hardeners. Examples of such hardeners have been described, for example, in German Offenlegungsschrift No. 2,263,602 and British Patent Specification No. 1,266,655. The layers may also be hardened by the process according to German Offenlegungsschrift No. 2,218,009 to produce color photographic materials suitable for high temperature processing.

The photographic layers or color photographic multilayered materials may also be hardened with hardeners of the diazine, triazine or 1,2-dihydroquinoline series as described in British patent specifications Nos. 1,193,290; 1,251,091; 1,306,544 and 1,266,655; French Patent Specification No. 7,102,716 or Belgian Patent No. 816 410. Examples of such hardeners include diazine derivatives containing alkyl or aryl sulfonyl groups; derivatives or hydrogenated diazines or triazines, e.g. 1,3,5-hexahydrotriazine, fluoro-substituted diazine derivatives, e.g. fluoropyrimidines, and esters of 2-substituted 1,2-dihydroquinoline and 1,2-dihydroisoquinoline-N-carboxylic acids. Vinyl sulfonic acid hardeners, carbodiimide hardeners and carbamoyl hardeners are also suitable, e.g. those described in German Offenlegungsschrift No. 2,263,602; British Patent Nos. 1 383 630 and 1 255 787; French Patent Specification No. 1,491,807; German Patent Specification No. 872,153 and DDR Patent Specification No. 7,218. Other suitable hardeners have been described, for example, in British patent specification No. 1,268,550.

The materials according to the invention may be, for example, positive, negative or reversal materials mounted on the usual support layers used in known manner for the production of photographic materials. Suitable substrates include e.g. foils of cellulose nitrate; cellulose acetate such as cellulose triacetate; polystyrene polyesters such as polyethylene terephthalate; polyolefines such as polyethylene or polypropylene; baryta paper substrates or polyolefine laminated paper substrates e.g. polyethylene laminated substrates, as well as glass.

Examples

The DIR compounds are preferably used in multilayered combinations of the kind employed, for example, for the production of light-sensitive negative or positive photographic color materials.

The effect of the DIR compounds according to the invention will now be illustrated by way of the example of a typical layer combination or partial layers thereof used for color negative materials.

Light-sensitive photographic material:

Arrangement of layers

Support: Substrated cellulose triacetate support.
a. Intermediate gelatine layer ($1\mu$)
b. Cyan layer consisting of an emulsion sensitized to the red spectral region and a color coupler for cyan (silver application: 4 g of $Ag/m^2$);
c. Intermediate gelatine layer ($1\mu$);
d. Magenta layer consisting of an emulsion sensitized to the green spectral region and a color coupler for magenta (silver application: 3.5 g of $Ag/m^2$);
e. Intermediate layer of gelatine ($1\mu$);
f. Yellow filter layer ($2\mu$);
g. Yellow layer consisting of an emulsion sensitized to the blue spectral region and a color coupler for yellow (silver application: 1.5 g of $Ag/m^2$);
h. Protective layer of gelatine ($1\mu$).

The material was hardened in the usual manner, e.g. with trisacryloylhexahydrotriazine. The individual red b, green d and cyan g sensitive partial layers were prepared by casting the following solutions:

b. 1 kg of a red sensitized silver halide emulsion (100 g of Ag/kg of emulsion) in which the silver halide consists of 98 mol % of silver bromide and 2 mol % of silver iodide, 50 ml of a 1% solution of 1,3,3a,7-tetraza-4-hydroxyl-6-methylindene in methanol;

360 g of a component dispersion of a solution of 15 g of cyan coupler of the following formula

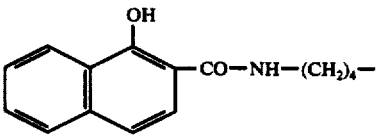

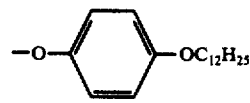

in 7.5 g of dibutyl phthalate and 30 g of diethylcarbonate,
100 ml of a 4% aqueous gelatine solution and 0.8 g of Mersolat (wetting agent, sulfonated paraffin hydrocarbons),
10 ml of a 10% aqueous saponin solution and 1000 ml of water.

d. The composition of the casting solution for the green sensitive layer was similar to that of the red sensitive layer b. except that the emulsion was sensitized to the green region of the spectrum and instead of the cyan coupler dispersion it contained 192 g of a dispersion of magenta coupler of the following formula

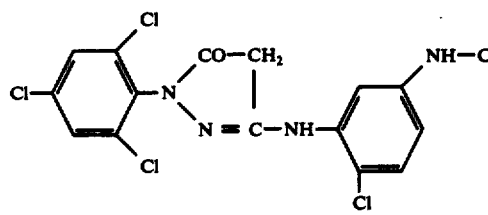

in a similar composition to that of the cyan emulsion in layer b.

g. The composition of the casting solution for the blue sensitive layer was similar to that of the red sensitive layer b, except that the emulsion was sensitized only to the blue region of the spectrum and instead of the cyan coupler dispersion it contained 175 g of a 5% solution of yellow coupler of the following formula

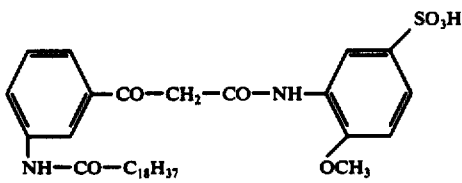

in an aqueous 8% gelatine solution.

The gelatine layers a, c, e and h were prepared by casting the following solution:
125 ml of a 10% gelatine solution,
500 ml of water
5 ml of a 10% aqueous solution of saponin The casting solution for the yellow filter layer f was the same as the casting solution for gelatine layers a, c, e and h, except that it also contained 1.4 g of finely dispersed metallic silver as is usual for barrier filters for the blue spectral portion of light.

Processing

The material was exposed behind a grey step wedge and successive colour separation filters blue, green and red in a conventional sensitometer and then developed in a color developer of the following composition:
2 g of sodium salt of isopropanoldiaminotetracetic acid
30 g of potash,
4 g of potassium sulfite,
1.5 g of potassium bromide,
2 g of hydroxylamine,
5 g of color developer of the following formula

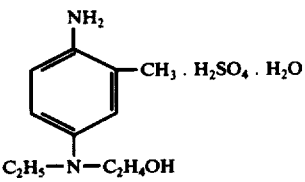

made up to 1 liter. pH adjusted to 10.2. The development time was 3¼ minutes at 38° C.

The subsequent processing stages indicated below were each carried out for 3¼ minutes. The bath temperature was again 38° C in each case.

Short stop bath:
30 ml of acetic acid (concentrated),
20 g of sodium acetate,
made up to 1 liter with water
Washing
Bleaching bath:
100 g of potassium ferricyanide,
15 g of potassium bromide,
made up with wter to 1 liter
Washing
Fixing bath:
20% aqueous solution of sodium thiosulfate
Final washing.

EXAMPLE 1

Incorporation of DIR compound 1 in red sensitive layer b DIR compound 1 is dispersed as follows:

A solution of 4.9 g of compound No. 1 in 3 g of tricresyl-phosphate and 12 ml of ethyl acetate was emulsified in a solution of 100 ml of a 4% aqueous gelatine solution and 0.8 g of Mersolat (wetting agent; sulfonated paraffin hydrocarbons) with vigorous stirring in a mixing siren.

Arrangement of layers: consisting of layers a, b and c.
Sample 1: no DIR compound in layer b
Sample 2: layer b contained DIR compound 1.

The dispersion of DIR compound 1 was added to the casting solution for the layer in a quantity of 42 g of dispersion to 1 kg of emulsion.

The samples were exposed to red light behind a step wedge and developed as described above. The inhibitory action of the DIR compound caused a regression of the gradation from $\gamma = 1.49$ (Sample 1) to $\gamma = 0.65$ (Sample 2). When the quantities of silver halide and color coupler were reduced in the preparation of the comparison sample without DIR compound (Sample 1a) so that the gradation is also $\gamma = 0.65$, is was found that the graininess of Sample 2 containing the DIR compound was substantially lower than in Sample 1a in spite of the same gradation and at least equal sensitivity:

|  | Sample 1a | Sample 2 |
| --- | --- | --- |
| Graininess $\delta D.10^{-2}$ at density $D = 1$ | 2.4 | 1.2 |
| Density of fog | 0.35 | 0.19 |

The graininess is given in $\delta_D$-values (rms values using a shutter diameter of 29 $\mu$) according to the method described by H. T. Buschmann in "Bestimmung der Körnigkeit photographischer Schichten mit Hilfe digitaler Technik" in Optik 38, 1973, pages 169 to 219.

It is characteristic of the DIR compounds according to the invention that they produce a marked reduction in fog although the compounds contain no free mercaptan.

EXAMPLE 2

Incorporation of DIR compound 10 in intermediate gelatine layer c.

DIR compound 10 was emulsified as indicated in Example 1.

A complete arrangement of layers (layers a to h) was prepared in which DIR compound 10 was incorporated in the intermediate gelatine layer c) that is to say between the red sensitive layer and the green sensitive layer (Sample 1). The casting solution for the modified gelatine layer c had the following composition:

50 ml of a 10% gelatine solution,
33 g of emulsion of DIR compound 10,
500 g of water,
7 ml of a 10% aqueous solution of saponin.

Layer c. was applied in a thickness of 1.5 μ.

A complete arrangement of layers with normal intermediate gelatine layer c was prepared for comparison (Sample 2).

The samples were exposed to red, green and white light behind a step wedge and processed as described above.

The results show that on exposure to red light, i.e. development of the cyan layer b, development of the magenta layer d which occurred to a certain extent in Sample 2 is completely prevented by the presence of the DIR compound. In the same way, the presence of DIR compound in the intermediate layer c completely prevented development of the cyan layer b on exposure to green light, i.e. development of the magenta layer d. The DIR compound combines with the developer oxidation product diffusing from adjacent layers and enters into a coupling reaction with it to release an inhibitor which diffuses into the adjacent red sensitive and green sensitive layers where it inhibits development. This results in an interimage effect (IIE) which can be defined by the following equation:

$$IIE = \frac{\gamma S - \gamma w}{0.6} \cdot 100\%$$

s = selective exposure
w = white exposure

Since the photographic materials used for the experiments are not masked, the side densities of the dyes interfere with the true determination of the interimage effect. To eliminate this interference, gradation curves are plotted from the analytical densities obtained by conversion of the measured integral densities. The γ-values were obtained from these gradation curves.

|  | IIE % | | Red exposure | Green exposure | White exposure | |
|---|---|---|---|---|---|---|
|  | cyan | magenta | cyan $\gamma_s$ | magenta $\gamma_s$ | cyan $\gamma_w$ | magenta $\gamma_w$ |
| Sample 1 | 82 | 52 | 1.02 | 0.86 | 0.53 | 0.55 |
| Sample 2 | 30 | 20 | 1.35 | 1.29 | 1.17 | 1.17 |

The Table clearly shows that the DIR compound incorporated in the intermediate gelatine layer c considerably increases the IIE value both in the cyan layer and in the magenta layer.

EXAMPLE 3

Incorporation of DIR compound in magenta layer d) of total layer combinations (Layers a to h):

DIR Compound 7 and, for comparison, known compounds A (from German Offenlegungsschrift No. 2,405,422) and B (from German Offenlegungsschrift No. 2,359,295) were used in comparable molar quantities. DIR compounds 7 and B were emulsified as described in Example 1. Compound A was dissolved in dimethylformamide. Comparable molar quantities of emulsions or solutions of DIR compounds were added to the casting solution for layer d) (e.g. Sample 1, DIR compound No. 7, 50 g of dispersion to 1 kg of silver halide emulsion). Sample 4 contains to DIR compound in layer d).

The samples were exposed to red, green and white light behind a step wedge and developed as described above. Since the film is not masked, the analytical densities are used for plotting the gradation curves.

The activity of the DIR compounds can be seen from the magneta-γ-values for green exposure (magenta $\gamma_s$). The influence of the DIR compounds present in the magenta layer on the IIE value of the cyan layer was also investigated.

| | | IIE % | Exposure | | |
|---|---|---|---|---|---|
| | | | Red | Green | White |
| Sample | DIR compound | cyan | cyan $\gamma_s$ | magenta $\gamma_s$ | cyan $\gamma_w$ |
| 1 | 1 | 123 | 1.43 | 0.43 | 0.69 |
| 2 | A | 38 | 1.40 | 1.05 | 1.17 |
| 3 | B | 42 | 1.37 | 1.04 | 1.12 |
| 4 | — | 28 | 1.40 | 1.30 | 1.23 |

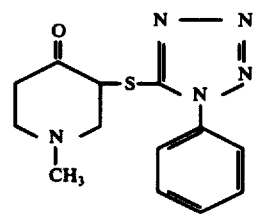

Compound A

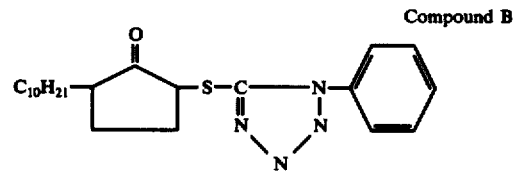

Compound B

It is clear from the table (magenta $\gamma_s$) that DIR compound 7 (Sample 1) has the most powerful inhibitory action, i.e. is most active in the magenta layer in which it is incorporated. The other DIR compounds are much less active. On exposure to white light, the inhibitor released from DIR compound No. 1 by development in the magenta layer and diffused into the cyan layer also powerfully inhibits development of the cyan layer so that a powerful cyan IIE (123%) is produced. DIR compounds A and B have much less effect in increasing the IIE in the adjacent cyan layer, which exists even without DIR coupler (Sample 4).

Similar results were obtained when any of the other compounds 1 to 11 is used instead of compound 3.

EXAMPLE 4

Incorporation of DIR compound 9 in the magenta layer and cyan layer of the total layer combination a – h:

The magenta partial color layer d was in this case arranged in two partial layers above one another on the double layer principle.

The lower partial layer d 1 contained a green sensitized silver halide emulsion in which the silver halide consists of 93 mol % of silver bromide and 7 mol % of silver iodide. This layer contained 35 g of the magenta coupler indicated above in 1 kg of emulsion.

The upper partial layer d 2 contained a more sensitive, coarser grained green sensitized silver halide emulsion in which the silver halide consisted of 95 mol % of silver bromide and 5 mol % of silver iodide. The proportion of magenta coupler in this layer was 10 g to 1 kg of emulsion.

The sensitivity of layer d 1 was lower by about 0.5 log I-t units than that of layer d 2.

DIR compound 9 was emulsified as described in Example 1 and added to layers d 1 (22 g of dispersion to 1 kg of silver halide) and b (20 g of dispersion to 1 kg of silver halide).

The sensitivity of the magenta double layer was higher by 0.1 log I-t units (measured at 0.2 density units above fog) than that of the individual magenta layer in the total layer combination of Example 3 for a comparable graininess.

| Sample | DIR compound | IIE (%) | | Exposure | | | |
| | | cyan | magenta | Red cyan s | Green magenta s | White cyan w | White magenta s |
|---|---|---|---|---|---|---|---|
| 1 | 9 in magenta and cyan | 63 | 50 | 1.00 | 1.02 | 0.62 | 0.72 |
| 2 | without DIR compound | 20 | 5 | 1.43 | 1.45 | 1.31 | 1.42 |

It can be seen from the Table that both a high magenta IIE value and a high cyan IIE value are obtained when the same DIR compound is used in the red sensitive and in the green sensitive partial colour layer. The side gradations of the magenta dye and of the cyan dye remain unchanged since the DIR couplers undergo practically colourless coupling.

We claim:

1. Light-sensitive photographic material having at least one silver halide emulsion layer containing a thioether compound which on reaction with the oxidation product of a color developer substance containing primary aromatic amino groups releases a diffusible mercaptan which inhibits development of the silver halide, wherein the improvement comprises the thioether compound is an oxazolinone-2 compound of the following formula or its tautomeric form:

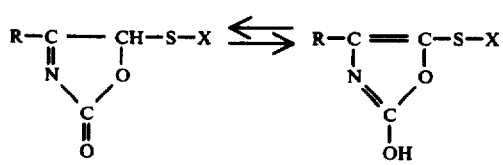

(I)

in which

X represents an alkyl group with 1 to 10 carbon atoms, which may be substituted by carboxyl and-/or amino groups, a phenyl group or a 5- or 6-membered heteroaromatic group having at least one nitrogen atom, R represents an alkyl group having from 1 to 18 carbon atoms which may be straight or branched chain or cyclic, and may be substituted by alkoxy, aroxy, aryl, halogen, carboxy or sulpho group, or phenyl or naphthyl groups which may be substituted by one or more substituents selected from the group consisting of alkyl, alkoxy, alkylamino or alkylthio groups, in any of which groups the alkyl portion may contain from 1 to 20 carbon atoms; nitro groups; halogen; carboxyl or sulpho groups; acyl or acylamino groups in either of which the acyl portion may be derived from carboxylic or sulphonic acids such as heptadecyl carbonamido; dimethylaminosulphonylphenyl; octadecylaminosulphonyl; methyloctadecylaminocarbonyl; phenylaminocarbonyl; benzoylaminophenoxycarbonyl or ethoxycarbonyl;

or a 5- or 6-membered heterocyclic group having at least one nitrogen atom whereby a mercapto group is splittable from the 5-position of the oxazolinone-2 compound.

2. Photographic material according to claim 1, wherein the group in its 4-position is an alkyl group having from 3 to 18 carbon atoms and the carbon atom which is linked to the 4-position of the oxazolinone-2 ring is a branched carbon atom.

3. Photographic material according to claim 1, wherein R is attached to the 4-position of the oxazolinone-2 ring via a saturated or aromatic carbon atom of the aliphatic, aromatic or heterocyclic group.

4. Photographic material according to claim 1, wherein X is a 1-phenyl tetrazolyl group.

5. Material according to claim 1, wherein the photographic material is a multilayered color photographic material and contains a thioether compound in at least one silver halide emulsion layer or in a light-insensitive layer of binder associated with it.

6. Process for the development of an imagewise exposed light-sensitive photographic material containing at least one silver halide emulsion layer including in an element of the material or in a processing bath a thioether compound which on reaction with the oxidation product of a color developer substance containing primary aromatic amino groups releases a diffusible mercaptan which inhibits development of the silver halide, the improvement according to which the thioether compound is an oxazolinone-2 compound from which a mercapto group can be split off from its 5-position said thioether compound is of the following formula or its tautomeric form:

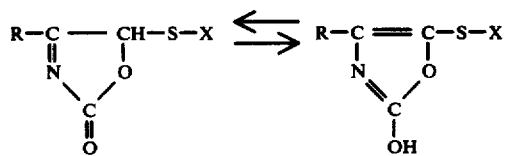

in which
- X represents an alkyl group with 1 to 10 carbon atoms, which may be substituted by carboxyl and/or amino groups, a phenyl or a 5- or 6-membered heteroaromatic group having at least one nitrogen atom,
- R represents an alkyl group having from 1 to 18 carbon atoms which may be straight or branched chain or cyclic, and may be substituted by alkoxy, aroxy, aryl, halogen, carboxy or sulpho group, or phenyl or naphthyl groups which may be substituted by one or more substituents selected from the group consisting of alkyl, alkoxy, alkylamino or alkylthio groups, in any of which groups the alkyl portion may contain from 1 to 20 carbon atoms; nitro groups; halogen; carboxyl or sulpho groups; acyl or acylamino groups in either of which the acyl portion may be derived from carboxylic or sulphonic acids such as heptadecyl carbon amido; dimethylaminosulphonylphenyl; octadecylaminosulphonyl; methyloctadecylaminocarbonyl; phenylaminocarbonyl; benzoylaminophenoxycarbonyl or ethoxycarbonyl; or a 5- or 6- membered heterocyclic group having at least one nitrogen atom.

7. Process according to claim 6 wherein the oxazolinone-2 compound is added to the developer or to a processing bath used before development.

* * * * *